(12) United States Patent
NarasimhaMurthy et al.

(10) Patent No.: US 12,299,172 B2
(45) Date of Patent: May 13, 2025

(54) METHODS AND APPARATUS FOR PROTECTING PATIENT INFORMATION DURING CHARACTERIZATION OF A SPECIMEN IN AN AUTOMATED DIAGNOSTIC ANALYSIS SYSTEM

(71) Applicant: Siemens Healthcare Diagnostics Inc., Tarrytown, NY (US)

(72) Inventors: Venkatesh NarasimhaMurthy, Hillsborough, NJ (US); Vivek Singh, Princeton, NJ (US); Yao-Jen Chang, Princeton, NJ (US); Benjamin S. Pollack, Jersey City, NJ (US); Ankur Kapoor, Plainsboro, NJ (US); Rayal Raj Prasad Nalam Venkat, Princeton, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/755,463

(22) PCT Filed: Oct. 22, 2020

(86) PCT No.: PCT/US2020/056917
§ 371 (c)(1),
(2) Date: Apr. 29, 2022

(87) PCT Pub. No.: WO2021/086719
PCT Pub. Date: May 6, 2021

(65) Prior Publication Data
US 2024/0169093 A1 May 23, 2024

Related U.S. Application Data

(60) Provisional application No. 62/929,062, filed on Oct. 31, 2019.

(51) Int. Cl.
*G06F 21/62* (2013.01)
*G06T 5/77* (2024.01)
(Continued)

(52) U.S. Cl.
CPC ............ *G06F 21/6254* (2013.01); *G06T 5/77* (2024.01); *G06T 7/0004* (2013.01); *G06T 11/60* (2013.01);
(Continued)

(58) Field of Classification Search
CPC ..... G06F 21/6254; G06T 5/77; G06T 7/0004; G06T 11/60; G06T 2207/20081;
(Continued)

(56) References Cited

U.S. PATENT DOCUMENTS 5,876,926 A * 3/1999 Beecham ............... G16H 10/40
422/402
9,322,761 B2 4/2016 Miller
(Continued)

FOREIGN PATENT DOCUMENTS

CN 105825509 A 8/2016
CN 106372390 A 2/2017
(Continued)

OTHER PUBLICATIONS

PCT International Search Report and Written Opinion dated Feb. 2, 2021 (12 Pages).
(Continued)

*Primary Examiner* — Mekonen T Bekele

(57) ABSTRACT

A method of characterizing a specimen and specimen container to be analyzed in an automated diagnostic analysis system. The method can provide a segmentation determination and/or an HILN determination (hemolysis, icterus, lipemia, or normal) of the specimen while protecting patient information. The method includes capturing an image of a
(Continued)

specimen container via an image capture device, identifying a label affixed to the specimen container in the captured image via an anonymization network, and editing the captured image via the anonymization network to mask some or all information present in the label so that it is removed from the captured image. Quality check modules and systems configured to carry out the method are also described, as are other aspects.

20 Claims, 5 Drawing Sheets

(51) Int. Cl.
*G06T 7/00* (2017.01)
*G06T 11/60* (2006.01)
(52) U.S. Cl.
CPC ............... *G06T 2207/20081* (2013.01); *G06T 2207/20084* (2013.01)
(58) Field of Classification Search
CPC .... G06T 2207/20084; G01N 35/00613; G01N 2035/00752; G01N 35/00732; G01N 2035/0406; G01N 35/04; G16H 10/60; G16H 10/40
See application file for complete search history.

(56) References Cited

U.S. PATENT DOCUMENTS

| | | | |
|---|---|---|---|
| 9,739,783 | B1 | 8/2017 | Kumar et al. |
| 10,198,832 | B2 | 2/2019 | De Fauw et al. |
| 2008/0195326 | A1 | 8/2008 | Munzer et al. |
| 2016/0078196 | A1 | 3/2016 | Malbon, Jr. et al. |
| 2016/0245833 | A1 | 8/2016 | Lefebvre |
| 2017/0364771 | A1 | 12/2017 | Pinheiro et al. |
| 2017/0372193 | A1* | 12/2017 | Mailhe ...................... G06T 5/77 |
| 2018/0045654 | A1 | 2/2018 | Park et al. |
| 2018/0129900 | A1* | 5/2018 | Kiraly .................... G06V 10/95 |
| 2019/0271714 | A1 | 9/2019 | Kluckner et al. |
| 2020/0151498 | A1 | 5/2020 | Sun et al. |
| 2021/0064927 | A1 | 3/2021 | Kluckner et al. |
| 2021/0133971 | A1 | 5/2021 | Ma et al. |
| 2021/0164965 | A1 | 6/2021 | Ma et al. |
| 2021/0334972 | A1 | 10/2021 | NarasimhaMurthy et al. |

FOREIGN PATENT DOCUMENTS

| | | | |
|---|---|---|---|
| CN | 106408562 | A | 2/2017 |
| CN | 108596166 | A | 9/2018 |
| EP | 3018482 | A1 | 5/2016 |
| JP | WO2002039341 | A * | 3/2004 |
| JP | WO2002039341 | A1 * | 3/2004 |
| JP | 2009-093538 | A | 4/2009 |
| JP | 2016-048530 | A | 4/2016 |
| JP | 2019500100 | A | 1/2019 |
| WO | 2016/112377 | A1 | 7/2016 |
| WO | 2017102827 | A1 | 6/2017 |
| WO | 2017106645 | A1 | 6/2017 |
| WO | 2017132168 | A1 | 8/2017 |
| WO | 2017132169 | A1 | 8/2017 |
| WO | 2018009405 | A1 | 1/2018 |
| WO | 2018039380 | A1 | 3/2018 |
| WO | 2018081617 | A2 | 5/2018 |
| WO | 2018089938 | A1 | 5/2018 |
| WO | 2018105062 | A1 | 6/2018 |
| WO | 2018/188023 | A1 | 10/2018 |
| WO | WO-2018191287 | A1 * | 10/2018 ........... A61B 5/7264 |
| WO | 2019/002521 | A1 | 1/2019 |
| WO | 2019/097327 | A1 | 5/2019 |
| WO | 2019/102043 | A1 | 5/2019 |
| WO | 2018/142764 | A1 | 11/2019 |
| WO | 2018/225448 | A1 | 7/2020 |

OTHER PUBLICATIONS

Tsui et al. Automatie Selective Removal of Embedded Patient Information From Image Content of DICOM Files. Apr. 30, 2012 (Apr. 30, 2012). [retrieved on Dec. 20, 2020]. Retrieved from the Internet: <URL: https://www.ajronline.org/doi/pdfplus/10.2214/AJR.10.6352> pp. 769-772.

Kushida et al. Strategies for de-identification and anonymization of electronic health record data for use in multicenter research studies. May 6, 2019 (May 6, 2019). [retrieved on Dec. 20, 2020]. Retrieved from the Internet: <URL: https:/fwww.ncbi.nlm.nih.gov/pmc/articles/PMC6502465/pdf/nihms-374697.pdJ> pp. 1-25.

Snyder et al. Effectiveness of Barcoding for Reducing Patient Specimen and Laboratory Testing Identification Errors: A Laboratory Medicine Best Practices Systematic Review and Meta-Analysis. Jul. 29, 2015 (Jul. 29, 2015). [retrieved on Dec. 20, 2020]. Retrieved from the Internet: <URL: https://www.ncbi.nlm.nih.gov/pmc/articles/PMC4518452/pdf/nihms692399.pdf>PQS, 1-45.

Liu et al., Image Inpainting for Irregular Holes Using Partial Convolutions. Dec. 15, 2018 (Dec. 15, 2018). arXiv: 1804.07723v2 [cs.CV], pp. 1-23.

Extended EP Search Report dated Nov. 17, 2022 of corresponding European Application No. 20880819.6, 4 Pages.

Clete A. Kushida et al: "Strategies for De-identification and Anonymization Of Electronic Health Record Data for Use in Multicenter Research Studies:", Medical Care, vol. 50, Jul. 1, 2012 (Jul. 1, 2012), pp. S82-S101, XP055439592, US, ISSN: 0025-7079, DOI: 10.1097/MLR.0b013e3182585355, the whole document.

Vimal Kumar Kasagani: "Optical quantification of hemolysis, icterus, and lipemia in human serum", Jan. 1, 2013 (Jan. 1, 2013), XP055530750, ISBN: 978-1-303-65004-8, Retrieved from the Internet: URL: http://cdmbuntu.lib.utah.edu/utils/getfile/collection/etd3/id/2642/filename/265.pdf, p. 4-p. 8.

Goodfellow, Ian, et al. "Generative adversarial nets." Advances in neural information processing systems 27 (2014) pp. 1-9.

Hideki, Aso et al. "Deep Representation Learning by Multi-Layer Neural Networks"; The Japanese Society for Artificial Intelligence; Year: Jul. 2013, vol. 28 No. 4, pp. 649-659.

Huang, Gao, et al. "Densely connected convolutional networks", Proceedings of the IEEE conference on computer vision and pattern recognition. 2017. pp. 4700-4708.

Jégou, Simon, et al. "The one hundred layers tiramisu: Fully convolutional densenets for semantic segmentation." Proceedings of the IEEE conference on computer vision and pattern recognition workshops. 2017.

Lecun, Yann et al. "Gradient-based learning applied to document recognition" Proceedings of the IEEE, New York, US, vol. 86, No. 11, Nov. 1, 1998, pp. 2278-2323, 1998 // ISSN: 0018-9219, DOI: 10.1109/5.726791.

Ren, Shaoqing et al: "Faster R-CNN: Towards Real-Time Object Detection with Region Proposal Networks"; IEEE Transactions on Pattern Analysis and Machine Intelligence; vol. 39, No. 6, Sep. 13, 2015; pp. 1137-1149; XP055473561; USA; ISSN:0162-8828; DOI: 10.1109/TPAMI.2016.2577031.

Shah Urmil et al: "A Review of Deep Learning Models for Computer Vision", 2018 IEEE PUNECON, IEEE, Nov. 30, 2018 (Nov. 30, 2018), pp. 1-6, XP033568970, DOI: 10.1109/PUNECON.2018.8745417.

* cited by examiner

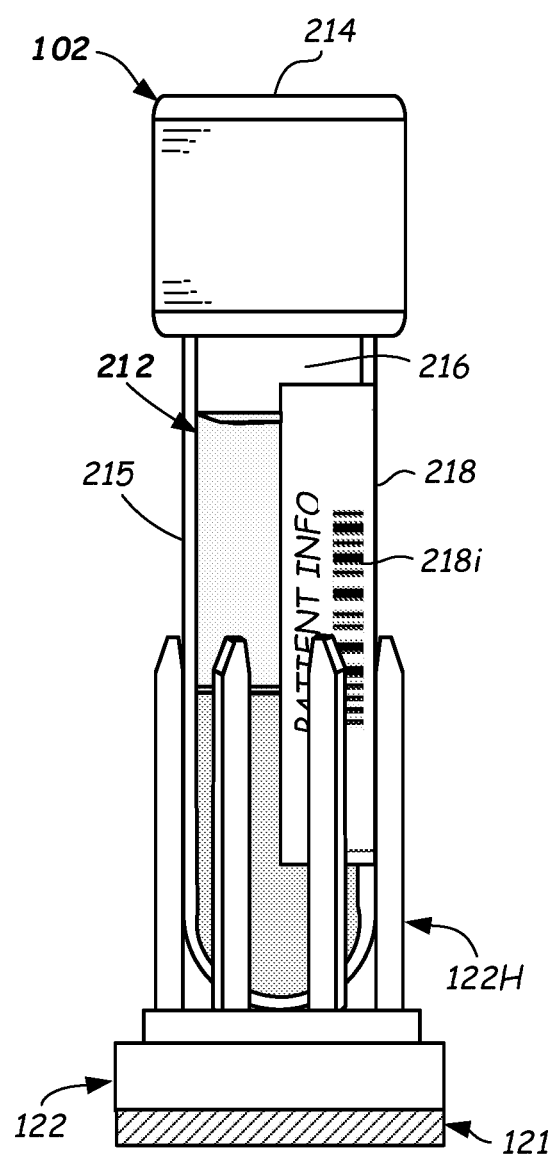
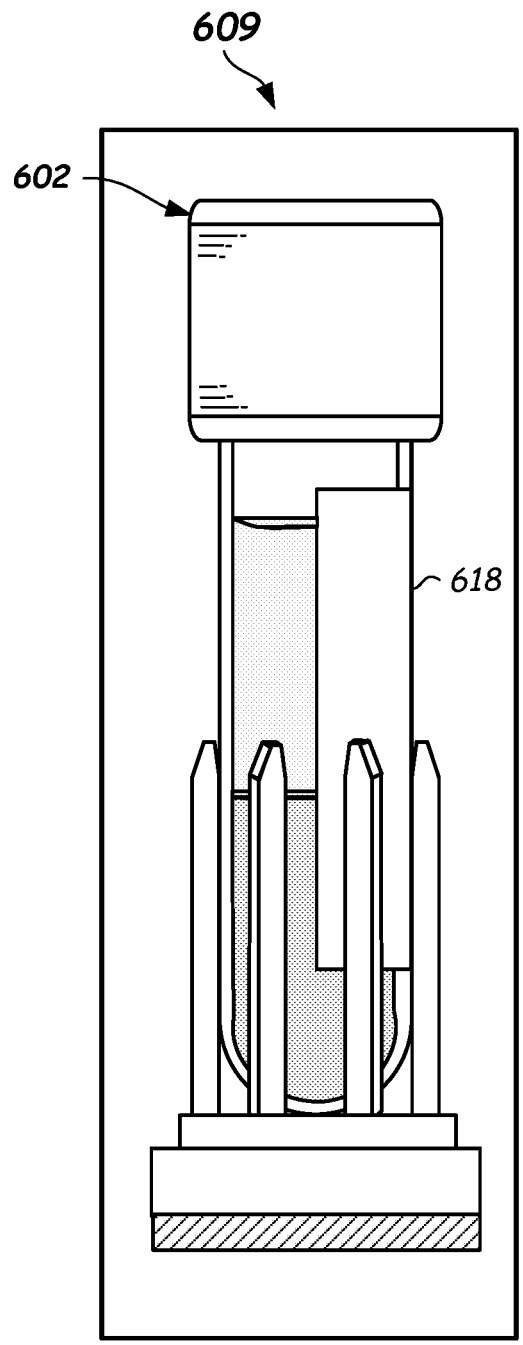
FIG. 3
FIG. 6

METHODS AND APPARATUS FOR PROTECTING PATIENT INFORMATION DURING CHARACTERIZATION OF A SPECIMEN IN AN AUTOMATED DIAGNOSTIC ANALYSIS SYSTEM

CROSS REFERENCE TO RELATED APPLICATION APPLICATIONS

This disclosure is a 371 of PCT/US2020/056917, filed Oct. 22, 2020, which claims priority to, and the benefit of, U.S. Provisional Patent Application No. 62/929,062, entitled "METHODS AND APPARATUS FOR PROTECTING PATIENT INFORMATION DURING CHARACTERIZATION OF A SPECIMEN IN AN AUTOMATED DIAGNOSTIC ANALYSIS SYSTEM," filed Oct. 31, 2019, the disclosures of which are hereby incorporated by reference in their entireties for all purposes.

FIELD

This disclosure relates to methods and apparatus for characterizing a specimen in an automated diagnostic analysis system.

BACKGROUND

Automated diagnostic analysis systems may analyze a specimen, such as, e.g., urine, blood serum, blood plasma, interstitial liquid, cerebrospinal liquid, and the like, to identify an analyte or other constituent in the specimen. Such specimens are usually contained within specimen containers (e.g., specimen collection tubes) that can be transported via an automated track to various pre-processing, pre-screening (including digital imaging), and analyzer stations within the automated diagnostic analysis system.

As part of the analysis, the specimen may be processed with one or more reagents and possibly other materials added therein, and then analyzed at one or more analyzer stations. After reaction, analytical measurements may be performed on the processed specimen via photometric or fluorometric readings by using a beam of interrogating radiation, by reading fluorescent or luminescent emissions, or the like. The analytical measurements allow determination of an amount of an analyte or other constituent in the specimen using well-known techniques.

In some instances, a presence of an interferent (e.g., hemolysis, icterus, and/or lipemia) in the specimen, which may result from a patient condition or sample pre-processing, may adversely affect test results of the analyte or constituent measurement obtained from one or more analyzers. For example, the presence of hemolysis (H) in the specimen, which may be unrelated to a patient's disease state, may cause a different interpretation of the disease condition of the patient. Similarly, the presence of icterus (I) and/or lipemia (L) in the specimen may also cause a different interpretation of the disease condition of the patient.

A pre-screening process for characterizing a specimen may thus be performed in the automated diagnostic analysis system. Pre-screening characterization of a specimen may include determining a presence of, and in some cases a degree of, an interferent, such as H, I, and/or L, in the specimen to be analyzed. Characterization of a specimen may also include a segmentation determination, which may identify various regions of the specimen container and specimen. This pre-screening process may be based on one or more images (e.g., digital images) of the specimen in a specimen container captured at one or more imaging stations (otherwise referred to as "quality check stations") of the automated diagnostic analysis system. The images may be stored in a computer memory.

However, along with the specimen and the specimen container, the images may also include images of one or more labels affixed to the specimen container. The one or more labels may contain printed or barcoded information that may include sensitive patient information (e.g., name, date of birth, address, patient number, and/or other personal information), along with other information such as tests to be performed, time and date specimen was obtained, medical facility information, tracking and routing information, etc.

SUMMARY

According to a first aspect, a method of characterizing a specimen in an automated diagnostic analysis system is provided. The method includes capturing an image of a specimen container with an image capture device, identifying a label affixed to the specimen container in the image with an anonymization network, and editing the image with the anonymization network to mask the identified label such that information present in the label is removed from the image to produce an edited image.

According to a second aspect, a method of characterizing a specimen container in an automated diagnostic analysis system is provided. The method includes capturing an image of a specimen container; identifying a label affixed to the specimen container in the image with an anonymization network of the automated diagnostic analysis system; and editing the image with the anonymization network to mask the label such that some or all information present on the label is removed from the image.

According to another aspect, a quality check module of an automated diagnostic analysis system is provided. The quality check module includes a plurality of image capture devices arranged around an imaging location configured to capture multiple images from multiple viewpoints of a specimen container, and a computer coupled to the plurality of image capture devices. The computer is configured and operative via programming instructions to input a captured image taken by one of the plurality of image capture devices to an anonymization network executing on the computer, wherein the captured image depicts at least a specimen container and a label affixed to the specimen container. The computer is also configured and operative via programming instructions to identify in the captured image the label affixed to the specimen container via the anonymization network, and edit the captured image via the anonymization network to mask an identified label such that some or all information, and particularly sensitive patient information, present in the label is removed from the captured image. The edited image may be output for segmentation or an interferent determination (e.g., HILN—hemolytic, icteric, lipemic, or normal) of a specimen in the specimen container via an HILN network executing on the computer.

Still other aspects, features, and advantages of this disclosure may be readily apparent from the following description and illustration of a number of example embodiments and implementations, including the best mode contemplated for carrying out the invention. This disclosure may also be capable of other and different embodiments, and its several details may be modified in various respects, all without departing from the scope of the disclosure. This disclosure is intended to cover all modifications, equivalents, and alternatives falling within the scope of the claims.

BRIEF DESCRIPTION OF THE DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

FIG. 3 illustrates a side view of the specimen container of FIG. 2 held in an upright orientation in a holder that can be transported on a track within the automated diagnostic analysis system of FIG. 1.

FIG. 6 illustrates an edited image of a specimen in a specimen container output from an anonymization network wherein information (e.g., patient information and a barcode) present on a label affixed to the specimen container has been masked and removed according to one or more embodiments.

DETAILED DESCRIPTION

Figure 1:
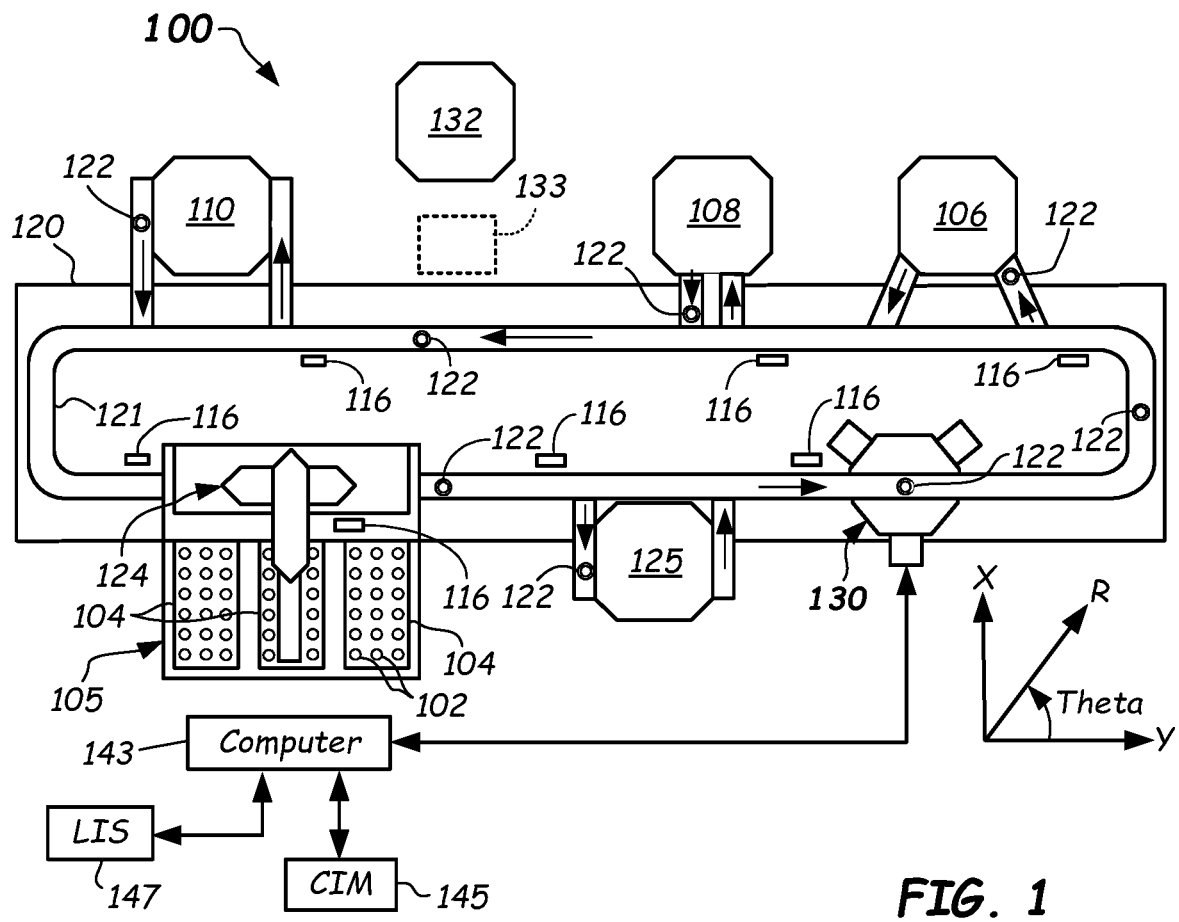
FIG. 1 illustrates a top schematic view of an automated diagnostic analysis system including one or more quality check modules configured to carry out imaging and label anonymization, as well as segmentation and/or HILN (hemolytic, icteric, lipemic, normal) determination methods according to one or more embodiments.

Patient privacy may potentially be compromised by having patient information included in stored images of a specimen container. Accordingly, there is an unmet need to provide methods, systems, and apparatus allowing characterization of a specimen in a specimen container, while protecting patient information that may be present in one or more labels affixed to the specimen container in an automated diagnostic analysis system.

Pre-screening of a specimen contained in a specimen container may be performed automatically at a quality check module of an automated diagnostic analysis system. Pre-screening in accordance with one or more embodiments may include capturing one or more images (e.g., one or more digital images) of the specimen contained in the specimen container at an imaging station (e.g., of a quality check module), editing the captured images to mask patient information that may be present in one or more labels affixed to the specimen container without affecting the imaged fluid characteristics of the specimen, and storing the edited images in a computer memory or database (wherein none of the originally-captured images depicting label information are stored). Then, using the edited images, the pre-screening may automatically perform a segmentation determination and/or an HILN determination. The segmentation determination may identify various regions of the specimen container and specimen, such as, e.g., a serum or plasma portion, a settled blood portion, a gel separator (if used), an air region, one or more label regions, a type of specimen container (indicating, e.g., height and width/diameter), and/or a type and/or color of a specimen container cap. The HILN determination may determine the presence of and, in some embodiments, the degree of an interferent in a serum or plasma portion of a blood specimen, or whether the specimen is normal (N), which indicates that the specimen includes either an acceptably low amount of an interferent or none at all.

The interferent may be hemolysis (H), icterus (I), or lipemia (L). Hemolysis may be defined as a condition in the serum or plasma portion wherein red blood cells are destroyed during pre-processing, which leads to the release of hemoglobin from the red blood cells into the serum or plasma portion such that the serum or plasma portion takes on a reddish hue. The degree of hemolysis may be quantified by assigning a hemolytic index (e.g., H0-H6 in some embodiments and more or less in other embodiments). Icterus may be defined as a condition of the blood where the serum or plasma portion is discolored dark yellow, which may be caused by an accumulation of bile pigment (bilirubin). The degree of icterus may be quantified by assigning an icteric index (e.g., I0-I6 in some embodiments and more or less in other embodiments). Lipemia may be defined as a presence in the blood of an abnormally high concentration of emulsified fat, such that the serum or plasma portion has a whitish or milky appearance. The degree of lipemia may be quantified by assigning a lipemic index (e.g., L0-L4 in some embodiments and more or less in other embodiments). In some embodiments, the pre-screening process may include determination of an un-centrifuged (U) class for a serum or plasma portion of a specimen that has not been centrifuged.

A quality check module of an automated diagnostic analysis system configured to execute a pre-screening characterization method may include an anonymization network and an HILN network, each implemented via programming instructions executable in a computer of the quality check module. The anonymization network may be a General Adversarial Network (GAN) or a Variational Auto Encoder (VAE). Alternatively, the anonymization network may be any suitable machine learning algorithm or method capable of image inpainting so as to mask some or all of the information on the label. In particular, patent information may be inpainted. An example anonymization network that may be suitable is described in "Image Inpainting For Irregular Holes Using Partial Convolutions," Guilin Liu et al., NVIDIA Corporation, Version 2, last revised Dec. 15, 2018, which is hereby incorporated herein by reference.

The anonymization network in accordance with one or more embodiments may be configured to inpaint the one or more labels in a captured image of a specimen and specimen container in order to mask (remove, replace, or erase) all barcodes and printed text on the one or more labels, while preserving the imaged fluid characteristics of the specimen such that the edited image will not affect a subsequent specimen segmentation and/or HILN determination. The one or more inpainted labels in the edited image may appear as a plain white label in the edited image, although other colors are possible. In some embodiments, the anonymization network is configured to reconstruct/generate an image of the specimen and specimen container without any label. In some embodiments, the anonymization network may be configured to report errors in the event a captured image has no specimen container depicted therein and/or a missing barcode and/or label. In some embodiments, the anonymization network may be configured to remove some of the noise in a captured image caused by, e.g., variations in machine/camera setup and/or calibration.

The quality check module of an automated diagnostic analysis system may also include an HILN network, which may be, e.g., a segmentation convolutional neural network (SCNN), that receives as input one or more edited images from the anonymization network. An SCNN may include, in some embodiments, greater than 100 operational layers including, e.g., BatchNorm, ReLU activation, convolution (e.g., 2D), dropout, and deconvolution (e.g., 2D) layers to extract features, such as simple edges, texture, and parts of the serum or plasma portion and label-containing regions. Top layers, such as fully convolutional layers, may be used to provide correlation between parts. The output of the layer may be fed to a SoftMax layer, which produces an output on a per-pixel (or per-patch—including n×n pixels) basis concerning whether each pixel or patch includes HILN. In some embodiments, only an output of HILN may be provided by the SCNN. In other embodiments, the output of the SCNN may include greater than 20 classes of HILN, so that for each interferent present, an estimate of the level (index) of the interferent is also obtained. The SCNN may also include a front-end container segmentation network (CSN) to determine a container type and a container boundary. More particularly, the CSN may classify (or "segment") various regions of the specimen container and specimen such as a serum or plasma portion, settled blood portion, gel separator (if used), air region, one or more label regions, type of specimen container (indicating, e.g., height and width/diameter), and/or type and/or color of a specimen container cap. A specimen container holder or background may also be classified. Alternatively, other types of HILN networks may be used.

Should the specimen be found to contain one or more of H, I, and L, a suitable notice may be provided to the operator, and/or the specimen container may be taken off line (1) to perform a remediation to rectify the one or more of the H, I, or L, (2) to redraw the specimen, or (3) to perform other processing. Thus, the ability to pre-screen for HILN before analysis by one or more analyzers may advantageously (a) minimize time wasted analyzing specimens that are not of the proper quality for analysis, (b) avoid or minimize erroneous test results, (c) minimize patient test result delay, and/or (d) avoid wasting of patient specimen, all while protecting patient information. Incorrect/low confidence sample specimens may be stored in a local database or in a cloud-based system.

Further details of inventive characterization methods, quality check modules configured to carry out the inventive characterization methods, and automated diagnostic analysis systems including one or more quality check modules will be further described with reference to FIGS. 1-7 herein.

Figure 2:
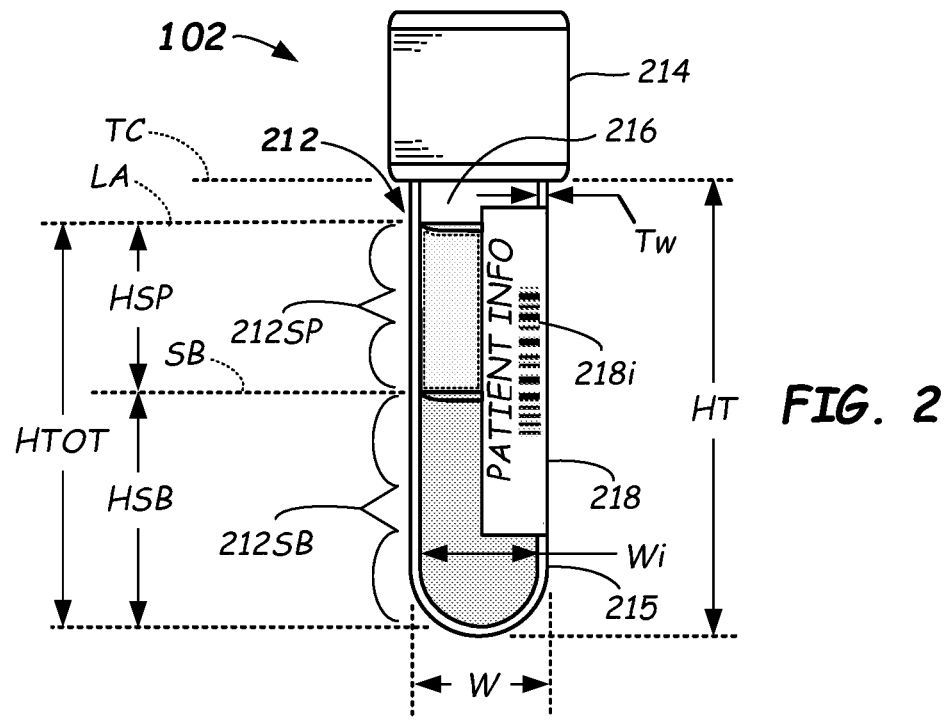
FIG. 2 illustrates a side view of a specimen container including a separated specimen with a serum or plasma portion that may contain an interferent and that further contains a label containing patient information and/or a barcode thereon.

FIG. 1 illustrates an automated diagnostic analysis system 100 capable of automatically processing multiple specimen containers 102 containing specimens 212 (see FIG. 2). The specimen containers 102 may be provided in one or more racks 104 at a loading area 105 prior to transportation to, and analysis by, one or more analyzers (e.g., first analyzer 106, second analyzer 108, and/or third analyzer 110) arranged about the automated diagnostic analysis system 100. More or less numbers of analyzers may be in the system. The analyzers may be any number of or combination of clinical chemistry analyzers, assaying instruments, and/or the like. The specimen containers 102 may be any suitably transparent or translucent container, such as a blood collection tube, test tube, sample cup, cuvette, or other clear or opaque glass or plastic container capable of containing and allowing imaging of the specimen 212 contained therein. The specimen containers 102 may be varied in size.

Specimens 212 (see FIG. 2) may be provided to the automated diagnostic analysis system 100 in the specimen containers 102, which may be capped with a cap 214. The caps 214 may be of different types and/or colors (e.g., red, royal blue, light blue, green, grey, tan, yellow, or color combinations), which may have meaning in terms of what test the specimen container 102 is used for, the type of additive included therein, whether the container includes a gel separator, or the like. Other colors may be used. In one embodiment, the cap type may be determined by the characterization method described herein.

Each of the specimen containers 102 may be provided with one or more labels 218 that may include identification information 218$i$ (i.e., indicia) thereon, such as a barcode, alphabetic characters, numeric characters, or combinations thereof. The identification information 218$i$ may include, e.g., patient information (e.g., name, date of birth, address, and/or other personal information), tests to be performed, time and date specimen obtained, medical facility information, tracking and routing information, etc. Other information may also be included. The identification information 218$i$ may be machine readable at various locations about the automated diagnostic analysis system 100. The machine readable information may be darker (e.g., black) than the label material (e.g., white) so that it can be readily imaged. The identification information 218$i$ may indicate, or may otherwise be correlated, via a Laboratory Information System (LIS) 147, to a patient's identification as well as tests to be performed on the specimen 212. Such identification information 218$i$ may be provided on the label 218, which may be adhered to or otherwise provided on an outside surface of the tube 215. As shown in FIG. 2, the label 218 may not extend all the way around the specimen container 102 or all along a length of the specimen container 102 such that from the particular front viewpoint shown, a large part of a serum or plasma portion 212SP is viewable (the part shown dotted) and unobstructed by the label 218.

The specimen 212 may include the serum or plasma portion 212SP and a settled blood portion 212SB contained within the tube 215. Air 216 may be provided above the serum and plasma portion 212SP and a line of demarcation between them is defined as the liquid-air interface (LA). The line of demarcation between the serum or plasma portion 212SP and the settled blood portion 212SB is defined as a serum-blood interface (SB). An interface between the air 216 and cap 214 is defined as a tube-cap interface (TC). The height of the tube (HT) is defined as a height from a bottom-most part of the tube 215 to a bottom of the cap 214, and may be used for determining tube size. A height of the serum or plasma portion 212SP is HSP and is defined as a height from a top of the serum or plasma portion 212SP to a top of the settled blood portion 212SB. A height of the settled blood portion 212SB is HSB and is defined as a height from the bottom of the settled blood portion 212SB to a top of the settled blood portion 212SB at SB. HTOT is a total height of the specimen 212 and equals HSP plus HSB.

In more detail, automated diagnostic analysis system 100 may include a base 120 (FIG. 1) (e.g., a frame, floor, or other structure) upon which a track 121 may be mounted. The track 121 may be a railed track (e.g., a mono rail or a multiple rail), a collection of conveyor belts, conveyor chains, moveable platforms, or any other suitable type of conveyance mechanism. Track 121 may be circular or any other suitable shape and may be a closed track (e.g., endless track) in some embodiments. Track 121 may, in operation, transport individual ones of the specimen containers 102 to various locations spaced about the track 121 in carriers 122.

Carriers 122 may be passive, non-motored pucks that may be configured to carry a single specimen container 102 on the track 121, or optionally, an automated carrier including an onboard drive motor, such as a linear motor that is programmed to move about the track 121 and stop at pre-programmed locations. Other configurations of carrier 122 may be used. Carriers 122 may each include a holder 122H (see FIG. 3) configured to hold the specimen container 102 in a defined upright position and orientation (as shown). The holder 122H may include a plurality of fingers or leaf springs that secure the specimen container 102 on the carrier 122, but some may be moveable or flexible to accommodate different sizes of the specimen containers 102. In some embodiments, carriers 122 may leave from the loading area 105 after being offloaded from the one or more racks 104. The loading area 105 may serve a dual function of also allowing reloading of the specimen containers 102 from the carriers 122 to the loading area 105 after pre-screening and/or analysis is complete.

A robot 124 may be provided at the loading area 105 and may be configured to grasp the specimen containers 102 from the one or more racks 104 and load the specimen containers 102 onto the carriers 122, such as onto an input lane of the track 121. Robot 124 may also be configured to reload specimen containers 102 from the carriers 122 to the one or more racks 104. The robot 124 may include one or more (e.g., at least two) robot arms or components capable of X (lateral) and Z (vertical—out of the page, as shown), Y and Z, X, Y, and Z, or r (radial) and theta (rotational) motion. Robot 124 may be a gantry robot, an articulated robot, an R-theta robot, or other suitable robot wherein the robot 124 may be equipped with robotic gripper fingers oriented, sized, and configured to pick up and place the specimen containers 102.

Upon being loaded onto track 121, the specimen containers 102 carried by carriers 122 may progress to a first pre-processing station 125. For example, the first pre-processing station 125 may be an automated centrifuge configured to carry out fractionation of the specimen 212. Carriers 122 carrying specimen containers 102 may be diverted to the first pre-processing station 125 by inflow lane or other suitable robot. After being centrifuged, the specimen containers 102 may exit on an outflow lane, or otherwise be removed by a robot, and continue along the track 121. In the depicted embodiment, the specimen container 102 in carrier 122 may next be transported to a quality check module 130 to carry out pre-screening, as will be further described herein.

The quality check module 130 is configured to pre-screen and carry out the characterization methods described herein to automatically determine a presence of, and optionally an extent or degree of H, I, and/or L contained in a specimen 212 or whether the specimen is normal (N). If found to contain effectively-low amounts of H, I and/or L, so as to be considered normal (N), the specimen 212 may continue on the track 121 and then may be analyzed by the one or more analyzers (e.g., first, second, and/or third analyzers 106, 108, and/or 110) based on the test orders and respective test menus of the analyzers 106, 108, and/or 110. Thereafter, the specimen container 102 may be returned to the loading area 105 for reloading to the one or more racks 104.

In some embodiments, in addition to detection of HILN, segmentation of the specimen container 102 and specimen 212 may take place. From the segmentation data, post processing may be used for quantification of the specimen 212 (i.e., determination of HSP, HSB, HTOT, and determination of location of SB or SG, and LA). In some embodiments, characterization of the physical attributes (e.g., size—height and width/diameter) of the specimen container 102 may take place at the quality check module 130. Such characterization may include determining HT and W, and possibly TC, and/or Wi. From this characterization, the size of the specimen container 102 may be extracted. Moreover, in some embodiments, the quality check module 130 may also determine cap type, which may be used as a safety check and may catch whether a wrong tube type has been used for the test ordered. The color and/or shape of the cap 214 may be indicative of the type of chemical additive (anticoagulant, etc.) contained in the specimen container 102 which is used for the particular ordered test.

In some embodiments, a remote station 132 may be provided on the automated diagnostic analysis system 100 that is not directly linked to the track 121. For instance, an independent robot 133 (shown dotted) may carry specimen containers 102 containing specimens 212 to the remote station 132 and return them after testing/pre-processing. Optionally, the specimen containers 102 may be manually removed and returned. Remote station 132 may be used to test for certain constituents, such as a hemolysis level, or may be used for further processing, such as to lower a lipemia level through one or more additions and/or through additional processing, or to remove a clot, bubble or foam, for example. Other pre-screening using the HILN detection methods described herein may be accomplished at remote station 132.

Additional station(s) may be provided at one or more locations on or along the track 121. The additional station(s) may include a de-capping station, aliquoting station, one or more additional quality check modules 130, and the like.

The automated diagnostic analysis system 100 may include a number of sensors 116 at one or more locations around the track 121. Sensors 116 may be used to detect a location of specimen containers 102 on the track 121 by means of reading the identification information 218i, or like information (not shown) provided on each carrier 122. Any suitable means for tracking the location may be used, such as proximity sensors. All of the sensors 116 may interface with a computer 143, so that the location of each specimen container 102 may be known at all times.

The pre-processing stations and the analyzers 106, 108, and 110 may be equipped with robotic mechanisms and/or inflow lanes configured to remove carriers 122 from the track 121, and with robotic mechanisms and/or outflow lanes configured to reenter carriers 122 to the track 121.

Automated diagnostic analysis system 100 may be controlled by the computer 143, which may be a microprocessor-based central processing unit CPU, having a suitable memory and suitable conditioning electronics and drivers for operating the various system components. Computer 143 may be housed as part of, or separate from, the base 120 of the automated diagnostic analysis system 100. The computer 143 may operate to control movement of the carriers 122 to and from the loading area 105, motion about the track 121, motion to and from the first pre-processing station 125 as well as operation of the first pre-processing station 125 (e.g., centrifuge), motion to and from the quality check module 130 as well as operation of the quality check module 130, and motion to and from each analyzer 106, 108, 110. Operation of each analyzer 106, 108, 110 for carrying out the various types of testing (e.g., assay or clinical chemistry) may be provided locally by workstations and/or computers of the analyzers, which may communicate with the computer 143.

For all but the quality check module 130, the computer 143 may control the automated diagnostic analysis system 100 according to software, firmware, and/or hardware commands or circuits such as those used on the Dimension® clinical chemistry analyzer sold by Siemens Healthcare Diagnostics Inc. of Tarrytown, New York, and such control is typical to those skilled in the art of computer-based electromechanical control programming and will not be further described herein. Other suitable systems for controlling the automated diagnostic analysis system 100 may be used. The control of the quality check module 130 may also be provided by the computer 143, but in accordance with the inventive characterization methods described in detail herein.

The computer 143 as used for image processing and to carry out the characterization methods described herein may include a CPU or GPU, sufficient processing capability and RAM, and suitable storage. In one example, the computer 143 may be a multi-processor-equipped PC with one or more GPUs, 8 GB Ram or more, and a Terabyte or more of storage. In another example, the computer 143 may be a GPU-equipped PC, or optionally a CPU-equipped PC operated in a parallelized mode. MKL could be used as well, 8 GB RAM or more, and suitable storage.

Embodiments of the disclosure may be implemented using a computer interface module (CIM) 145 that allows a user to easily and quickly access a variety of control and status display screens. These control and status display screens may display and enable control of some or all aspects of a plurality of interrelated automated devices used for preparation and analysis of specimens 212. The CIM 145 may be employed to provide information about the operational status of a plurality of interrelated automated devices as well as information describing the location of any specimen 212 and a status of tests to be performed on, or being performed on, the specimen 212. The CIM 145 is thus adapted to facilitate interactions between an operator and the automated diagnostic analysis system 100. The CIM 145 may include a display screen operative to display a menu including icons, scroll bars, boxes, and buttons through which the operator may interface with the automated diagnostic analysis system 100. The menu may comprise a number of functional elements programmed to display and/or operate functional aspects of the automated diagnostic analysis system 100.

Figure 4A:
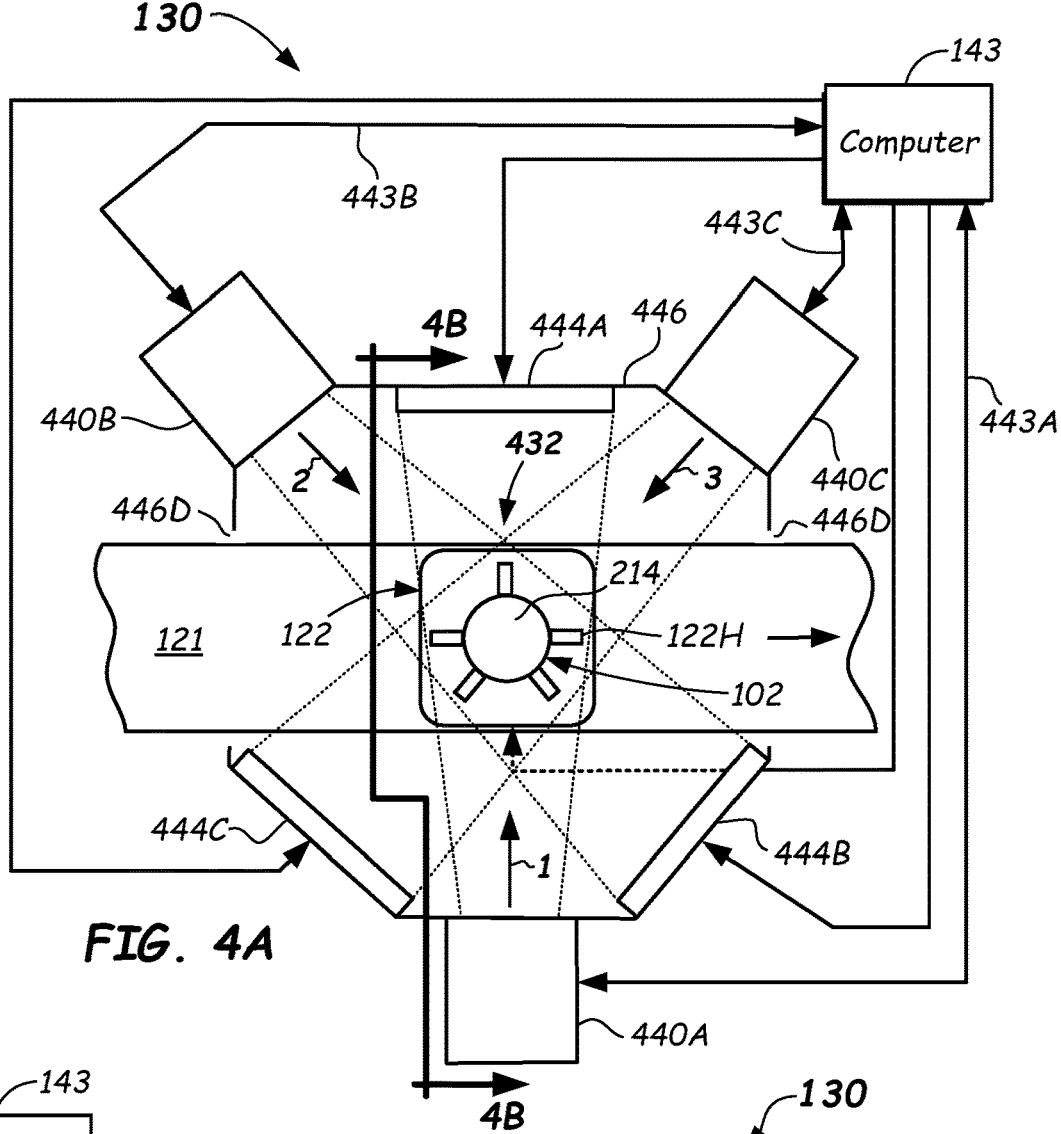
FIG. 4A illustrates a schematic top view of a quality check module (with top removed) including multiple viewpoints (e.g., viewpoints 1-3) and configured to capture and analyze multiple images to enable label anonymization as well as a segmentation and/or an HILN determination according to one or more embodiments.
Figure 4B:
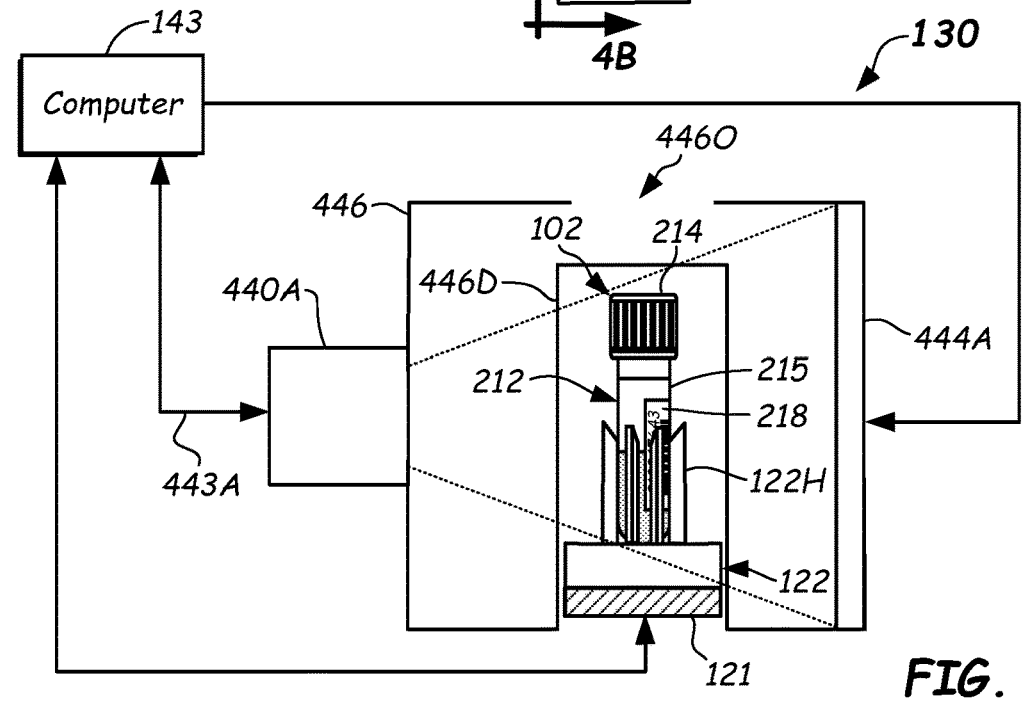
FIG. 4B illustrates a schematic side view of the quality check module (with front enclosure wall removed) of FIG. 4A taken along section line 4B-4B of FIG. 4A according to one or more embodiments.

FIGS. 4A and 4B show an embodiment of a quality check module 130 configured to carry out the characterization methods as shown and described herein. Quality check module 130 may be configured with programming instructions to pre-screen for a presence and degree of an interferent (e.g., H, I, and/or L) in a specimen 212 (e.g., in a serum or plasma portion 212SP thereof) prior to analysis by the one or more analyzers 106, 108, 110. Pre-screening in this manner allows for additional processing, additional quantification or characterization, and/or discarding and/or redrawing of a specimen 212 without wasting valuable analyzer resources or possibly having the presence of an interferent affect the veracity of the test results.

In addition to the interferent detection methods described herein, other detection methods may take place on the specimen 212 contained in the specimen container 102 at the quality check module 130. For example, a method may be carried out at the quality check module 130 to provide segmentation data. The segmentation data may be used in a post-processing step to quantify the specimen 212, e.g., to determine certain physical dimensional characteristics of the specimen 212, such as LA and SB, and/or determination of HSP, HSB, and/or HTOT. Quantification may also involve estimating, e.g., a volume of the serum or plasma portion (VSP) and/or a volume of the settled blood portion (VSB). Furthermore, the quality check module 130 may be used to quantify geometry of the specimen container 102, i.e., quantify certain physical dimensional characteristics of the specimen container 102, such as the location of TC, HT, and/or W or Wi of the specimen container 102. Other quantifiable geometrical features may also be determined.

Quality check module 130 may include a housing 446 that may at least partially surround or cover the track 121 to minimize outside lighting influences. The specimen container 102 may be located inside the housing 446 during the image-taking sequences. Housing 446 may include one or more doors 446D to allow the carriers 122 to enter into and/or exit from the housing 446. In some embodiments, the ceiling may include an opening 446O to allow a specimen container 102 to be loaded into or removed from the carrier 122 by a robot including moveable robot fingers from above.

As shown in FIGS. 4A and 4B, quality check module 130 may include multiple image capture devices 440A-440O configured to capture lateral images of the specimen container 102 and specimen 212 at an imaging location 432 from multiple viewpoints (viewpoints labeled 1, 2, and 3). While three image capture devices 440A-440C are shown and preferred, optionally two, four, or more can be used. The viewpoints 1-3 may be arranged so that they are approximately equally spaced from one another, such as about 120° from one another, as shown. The images may be taken in a round robin fashion, for example, where one or more images from viewpoint 1 may be taken followed sequentially by viewpoints 2 and 3. Other sequences of image taking may be used. Light sources 444A-444C may back light the specimen container 102 (as shown). Multiple viewpoints are advantageous because one or more images taken from viewpoints 1-3 may be partially or fully occluded (i.e., no clear view of the serum or plasma portion 212SP) by one or more labels 218.

As depicted, the image capture devices 440A, 440B, 440C may be arranged around the track 121. Other arrangements of the plurality of image capture devices 440A, 440B, and 440C may be used. In this way, the images of the specimen 212 in the specimen container 102 may be taken while the specimen container 102 is residing in the carrier 122 at the imaging location 432. The field of view of the multiple images obtained by the image capture devices 440A, 440B, and 440C may overlap slightly in a circumferential extent.

Image capture devices 440A-440O may be any suitable device for capturing well-defined digital images, such as conventional digital cameras capable of capturing a pixelated image, charged coupled devices (CCD), an array of photodetectors, one or more CMOS sensors, or the like. The captured image size may be, e.g., about 2560×694 pixels. In another embodiment, the image capture devices 440A, 440B, 440C may capture an image size that may be about 1280×387 pixels, for example. Other image sizes and pixel densities may be used.

Each image may be triggered and captured at quality check module 130 in response to receiving a triggering signal provided in communication lines 443A, 443B, and 443C from the computer 143. Each of the captured images may be processed by the computer 143 according to one or more embodiments. In one particularly effective method, high dynamic range (HDR) processing may be used to capture and process the image data from the captured images.

Figure 5:
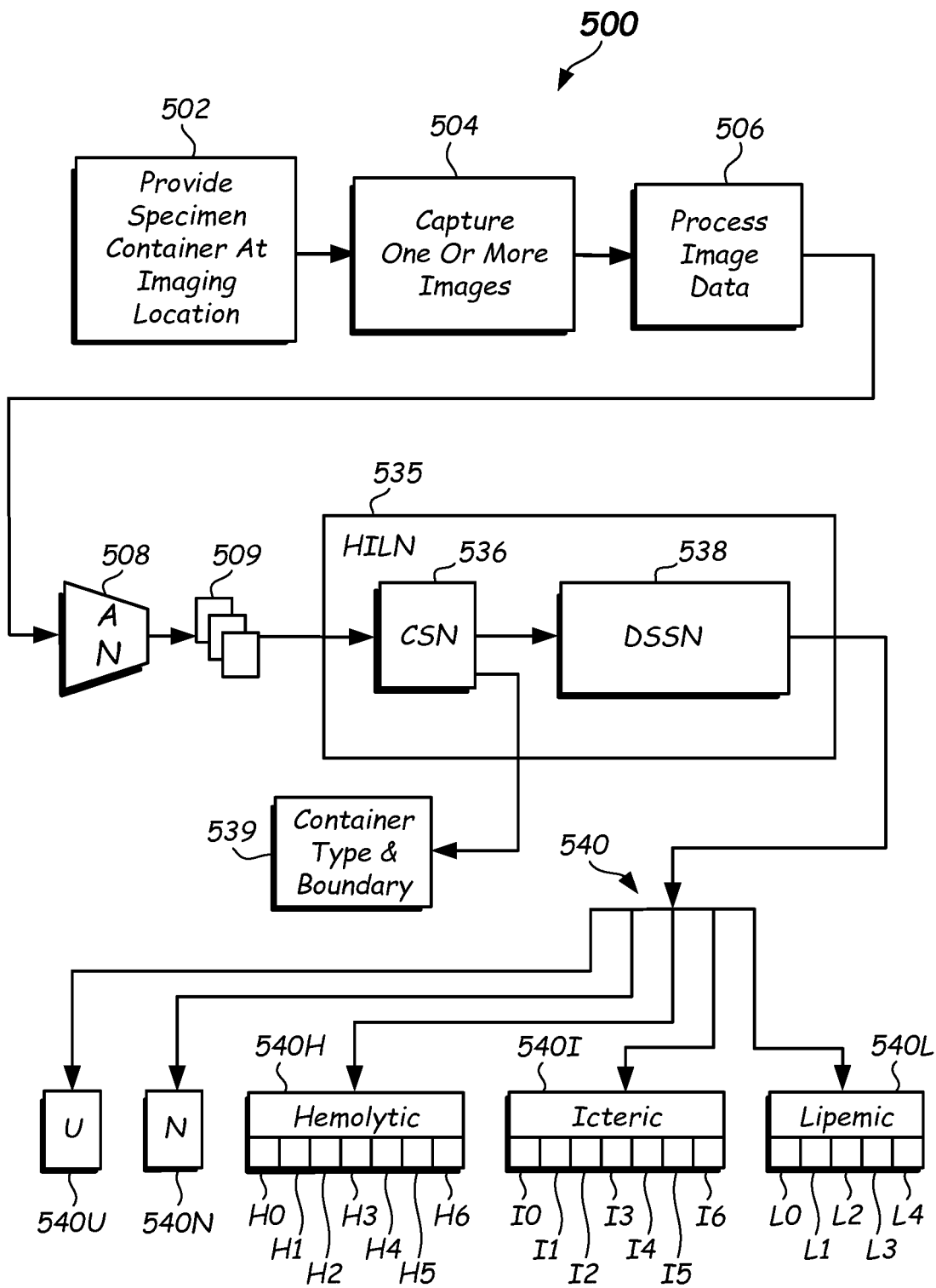
FIG. 5 illustrates a functional block diagram of an HILN network operative to output segmentation data and an interferent determination and classification index of a specimen in a specimen container and further including an anonymization network (AN) operative to edit a captured image in order to mask some or all information on the label according to one or more embodiments.

FIG. 5 shows a functional HILN network architecture 500 configured to carry out the characterization methods and label anonymization described herein. Functional architecture 500 may be implemented in a quality check module 130 and executed by the computer 143 via suitable programming instructions. As discussed above, the specimen container 102 may be provided at imaging location 432 (FIGS. 4A and 4B) of the quality check module 130 as represented at functional block 502. Multi-viewpoint images (e.g., from viewpoints 1, 2, and 3) of the specimen container 102 may be captured by the plurality of image capture devices 440A-440O as represented at functional block 504. The image data for each of the multi-viewpoint images may optionally be initially processed to provide a plurality of optimally-exposed and normalized image data sets (hereinafter "image data sets") as represented at functional block 506. The image data (i.e., pixel data) of a captured image of a specimen 212 (and specimen container 102) may be provided as input to an anonymization network 508 in accordance with one or more embodiments. In some embodiments, the various digital images from the multiple viewpoints may be digitally joined side-to-side to provide a 360 degree image including the one or more labels.

Anonymization network 508, which can be part of the quality check module 130, receives the image data sets of the captured images of a specimen container and specimen therein and identifies one or more labels that may be affixed to the specimen container in the captured images. Specimen containers are known to have different label configurations including different numbers of labels, degrees of overlap, and positioning (vertically and circumferentially). Anonymization network 508 may have been previously trained to identify the one or more labels 218 in the captured image via any label identification method. For example, a label configuration database may be used that includes label data on hundreds or even thousands of training images of specimen containers 102 having a variety of configurations of labels 218 captured during a training phase of anonymization network 508. Image caparison techniques may be used to compare and select the closest image. Image comparison can be a pixel-by-pixel comparison, wherein each and every pixel color in the captured image is compared to the equivalent pixel in the training images. If all pixel colors match both images are identical. The image comparison tool can have parameters to adjust such as a pixel/color tolerance, which can be set as a number of pixels that are allowed to differ between the two images. Thus, some differences between the training and captured images can be tolerated. Optionally, the Anonymization network 508 may include a trained convolutional neural network (CNN) that may be used to identify the label 218. Other suitable methods for defining the area or pixels in the images that are label 218 may be used. The training phase of the anonymization network 508 may be performed in the quality check module 130 prior to any pre-screening (characterization).

During later characterization, once the label is identified, anonymization network 508 may edit the captured image. The editing can mask the identified label via inpainting such that some or all of the information present in the label is removed from or otherwise replaced in the captured image. For example, the inpainting can be performed with the same color as the background of the label (white) by matching the color of the background of the identified label 218. Optionally, the entire identified area of the label 218 can be inpainted. Other techniques of masking to remove information present in a label may be used, such as redacting the label 218 in the image in a pattern, such as a wide line or lines, or with another color other than the background color of the label 218. Inpainting may be used to change the color of the pixels identified as label that previously containing patient information, such that the prior patent information is masked (removed). Moreover, anonymization network 508 preserves the imaged fluid characteristics of the specimen in the edited image such that subsequent specimen segmentation and/or HILN determination are not affected by the masking. Edited images 509 from anonymization network 508 may be stored in a computer memory or database of computer 143 and/or other storage location(s) and may be provided as input to an HILN network 535, which may perform segmentation and/or perform an HILN determination. The captured images (represented at functional block 504) and image data (represented at optional functional block 506) containing labels with patient information are not permanently stored in any ROM memory or database and are not accessible by HILN network 535 in order to protect patient information. Anonymization network 508 may be a General Adversarial Network (GAN), which is also sometimes referred to as a Generative Adversarial Network. GAN techniques learn to generate new data with the same statistics as the training set. For example, a GAN trained on photographs including labels can generate new image that looks like the label 218. Optionally, a Variational Auto Encoder (VAE) may be used or any other suitable machine learning algorithm capable of image inpainting or other suitable masking of image data.

FIG. 6 shows a display of an edited image 609 that may be output from anonymization network 508. Edited image 609 depicts a specimen container 602 having an inpainted (e.g., plain white) label 618 wherein some or all printed and barcoded information has been masked by being removed, replaced, inpainted, or redacted. Specimen container 102 of FIGS. 2 and 3, e.g., may have been the source object of a captured image provided as input to anonymization network 508 that resulted in edited image 609. In some embodiments, the edited image 609 may include images from multiple viewpoints that have been digitally stitched together (e.g., joined) to provide an enhanced image because the label was viewed from multiple viewpoints including part of the label.

Returning to FIG. 5, HILN network 535, which may be a segmentation convolutional neural network (SCNN) (other types of HILN networks may be employed to provide a segmentation and/or HILN determination), may provide a detailed characterization of an edited image of a specimen container, such as, e.g., specimen container 602. This may include, e.g., separation of the specimen container from its background and understanding of the serum or plasma portion's content. These tasks may be completed with HILN network 535, which can perform pixel-level classification.

Given an edited input image 509 (i.e., pixel data) from anonymization network 508, the HILN network 535 is operative to assign a classification index to each pixel of the image based on its local appearance as indicated by its pixel data value. The extracted pixel index information can be further processed by the HILN network 535 to determine a final HILN classification index for the serum or plasma portion 212SP. In some embodiments, the classification index may include 21 serum classes, including an un-centrifuged class, a normal class, and 19 HIL classes/subclasses, as described in more detail below.

A challenge to determining an HILN classification index may result from the small appearance differences within each sub-class of the H, I, and L classes. That is, the pixel data values of adjacent sub-classes are very similar. To overcome these challenges, the HILN network 535 may include a very deep semantic segmentation network (DSSN) 538 that includes, in some embodiments, more than 100 operational layers.

To overcome appearance differences that may be caused by variations in specimen container type (e.g., size and/or shape), the HILN network 535 may also include a container segmentation network (CSN) 536 at the front end of the DSSN 538. The CSN 536 is configured and operative to determine and output container type and boundary segmentation information 539, which may include, e.g., as applicable, locations, sizes, areas, and/or volumes of a serum or plasma portion 212SP, a settled blood portion 212SB, gel separator (if used), air region 216, one or more label regions 218, a type of specimen container (indicating, e.g., height and width/diameter), and/or a type and/or color of a specimen container cap 214. In some embodiments, the CSN 536 may have a similar network structure as the DSSN 538, but shallower (i.e., with far fewer layers).

As shown in FIG. 5, an output of the HILN network 535 may be a classification index 540 that, in some embodiments, may include an un-centrifuged class 540U, a normal class 540N, a hemolytic class 540H, an icteric class 540I, and a lipemic class 540L. In some embodiments, hemolytic class 540H may include sub-classes H0, H1, H2, H3, H4, H5, and H6. Icteric class 540I may include sub-classes I0, I1, I2, I3, I4, I5, and I6. And lipemic class 540L may include sub-classes L0, L1, L2, L3, and L4. Each of hemolytic class 540H, icteric class 540I, and/or lipemic class 540L may have, in other embodiments, other numbers of fine-grained sub-classes.

Figure 7:
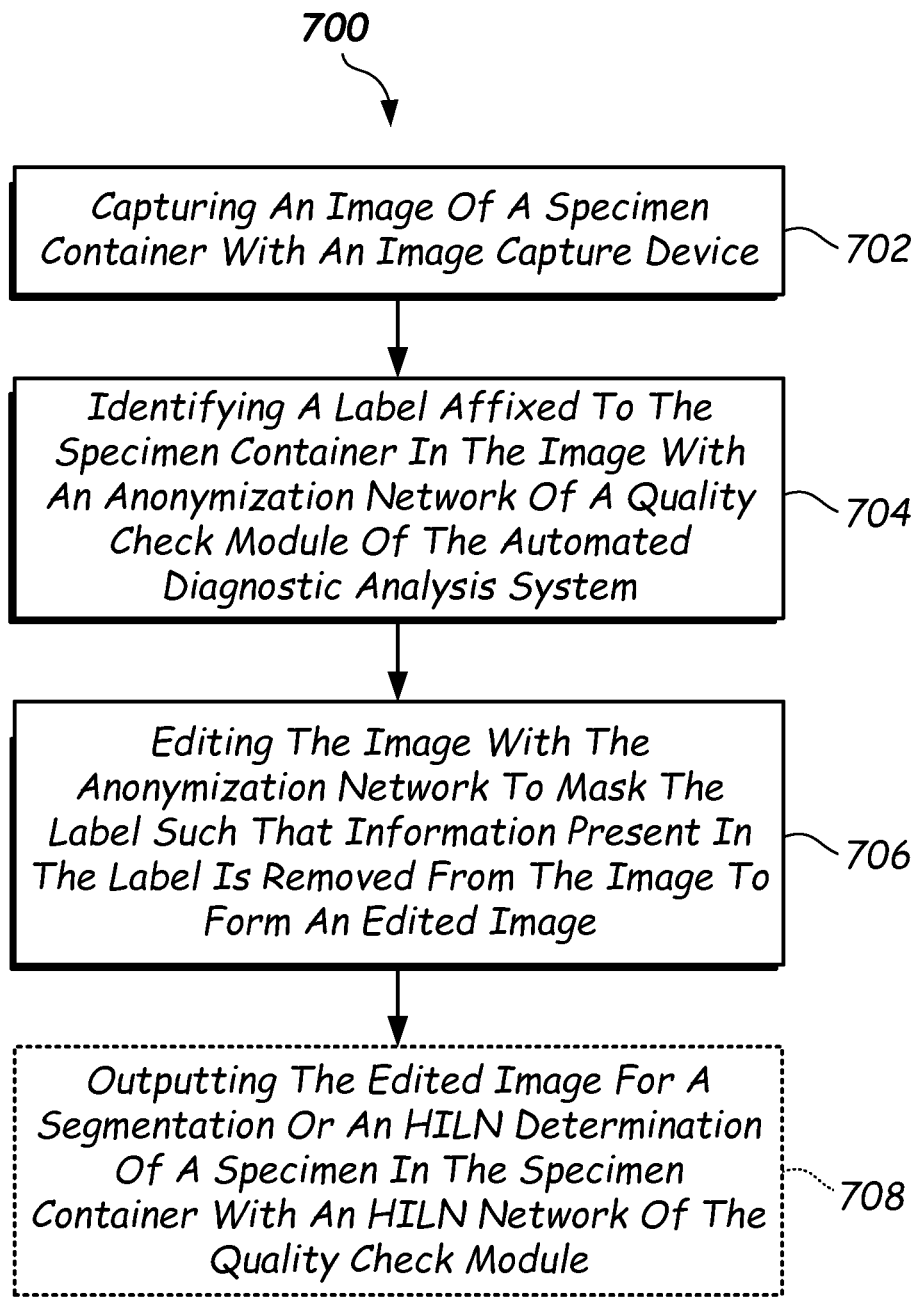
FIG. 7 is flowchart of a method of characterizing a specimen in an automated diagnostic analysis system including label anonymization according to one or more embodiments.

FIG. 7 illustrates a flowchart of a characterization method 700 according to one or more embodiments. The characterization method 700 may be carried out by quality check module 130 (in conjunction with computer 143 executing programming instructions) as described herein, and may include at process block 702, capturing an image of a specimen container via an image capture device. For example, images may be captured by one or more of image capture devices 440A-440C (of FIGS. 4A and 4B) wherein each may be a digital, pixelated image. The captured images may be processed individually or digitally joined as one captured image and processed.

The characterization method 700 may further include, in process block 704, identifying a label affixed to the specimen container in the captured image via an anonymization network of the quality check module, such as anonymization network 508 of FIG. 5.

In process block 706, the characterization method 700 may include editing the captured image via the anonymization network (e.g., anonymization network 508) to mask the identified label (e.g., label 218) such that some or all information present in the label is removed from the edited image. For example, referring to FIGS. 5 and 6, the edited image may be edited image 609, wherein imaged label 618 has been masked such that the printed and any barcoded information 218i that may have present on label 218 of a specimen container 102 (see FIGS. 2 and 3) is removed from the edited image. Removal may include inpainting or otherwise replacement of the pixels containing the printed and any barcoded information 218i. In some instances, removal may include redacting.

In process block 708, the characterization method 700 may include outputting the edited image for segmentation and/or an HILN (hemolytic, icteric, lipemic, normal) determination of a specimen in the specimen container via an HILN network of the quality check module. For example, as shown in FIG. 5, the output (e.g., edited images 509) of anonymization network 508 may be provided to HILN 535 for a segmentation and/or HILN determination. The HILN determination may be a classification index 540 (e.g., 540U, 540N, 540H, 540I, or 540L and, in some embodiments, may also include a sub-class, such as 540H (H0, H1, H2, H3, H4, H5, H6), 540I (I0, I1, I2, I3, I4, I5, I6), and 540L (L0, L1, L2, L3, and L4).

Accordingly, based on the foregoing it should be apparent that an improved characterization method 700 is provided that protects patient information during an automated segmentation and/or HILN determination.

As should also be apparent, the above characterization methods may be carried out using a quality check module (e.g., quality check module 130), comprising a plurality of image capture devices (e.g., image capture devices) 440A-440C arranged around an imaging location (e.g., imaging location 432), and configured to capture one or more images from one or more viewpoints (e.g., viewpoints 1-3 of FIG. 4A) of a specimen container 102 including one or more labels 218 and containing a specimen 212. The quality check module also includes a computer (e.g., computer 143) coupled to the plurality of image capture devices and configured to process pixel data of the one or more images. The computer (e.g., computer 143) may also be configured and capable of being operated to mask any information present in a label affixed to a specimen container depicted in the one or more captured images of the specimen and to provide an HILN determination based on one or more edited images of the specimen with the label information masked. In some embodiments, images including the information present in a label 218 are not permanently stored, and are only temporarily stored only as part of the identification and editing processes of blocks 704 and 706.

While the disclosure is susceptible to various modifications and alternative forms, specific method and apparatus embodiments have been shown by way of example in the drawings and are described in detail herein. It should be understood, however, that the particular methods and apparatus disclosed herein are not intended to limit the disclosure but, to the contrary, to cover all modifications, equivalents, and alternatives falling within the scope of the claims.

What is claimed is:

1. A method of characterizing a specimen in an automated diagnostic analysis system, comprising:
   capturing an image of a specimen container with an image capture device;
   identifying a label affixed to the specimen container in the image with an anonymization network, wherein the anonymization network is a pre-trained network trained, with training images, to identify labels on specimen containers; and editing the image with the anonymization network to mask the label such that information present in the label is removed from the image to produce an edited image, wherein information present in the label is removed by altering pixel data within the image.

2. The method of claim 1, wherein the anonymization network is part of a quality check module.

3. The method of claim 1, further comprising outputting the edited image for a segmentation or an HILN determination of the specimen in the specimen container with an HILN network of a quality check module.

4. The method of claim 1, wherein the anonymization network comprises a general adversarial network.

5. The method of claim 1, wherein the anonymization network comprises a variational auto encoder.

6. The method of claim 1, wherein the anonymization network is configured to inpaint the label in the image of the specimen and the specimen container in order to erase all barcodes and printed text on the label and form an inpainted label in the edited image.

7. The method of claim 6, wherein the inpainted label appears as a white label in the edited image.

8. The method of claim 1, wherein a segmentation convolutional neural network (SCNN) receives as input one or more edited images from the anonymization network.

9. The method of claim 1, further comprising training the anonymization network in a training phase prior to any characterization.

10. The method of claim 1, wherein the editing of the image with the anonymization network preserves imaged fluid characteristics of the specimen in the edited image.

11. The method of claim 1, wherein captured images containing labels with patient information are not permanently stored in order to protect patient information.

12. The method of claim 1, wherein the information is patient information.

13. The method of claim 1, wherein the editing of the image with the anonymization network removes all information present on the label.

14. The method of claim 1, further comprising capturing images of the specimen container from other viewpoints.

15. The method of claim 1, wherein the anonymization network is configured to inpaint the label in the image in order to mask all barcodes on the label.

16. The method of claim 1, wherein the anonymization network is configured to inpaint the label in the image in order to mask all printed text on the label.

17. A method of characterizing a specimen container in an automated diagnostic analysis system, comprising:

capturing an image of the specimen container, the image including fluid characteristics of a specimen within the specimen container;

identifying in the image a label affixed to the specimen container;

editing the image with an anonymization network to mask the label such that some or all printed information present on the label is removed from the image to form an edited image, wherein information present in the label is removed by altering pixel data representing the label and wherein pixel data representing imaged fluid characteristics of the specimen is preserved;

storing the edited image; and employing a characterization network to access the stored image and characterize at least one imaged fluid characteristic of the specimen, wherein the characterization network is trained to identify one or more fluid characteristics of the specimen within the image.

18. A quality check module of an automated diagnostic analysis system, comprising:

a plurality of image capture devices arranged around an imaging location configured to capture multiple images from multiple viewpoints of a specimen container; and a computer coupled to the plurality of image capture devices, the computer configured and operative via programming instructions to:

input a captured image taken by one of the plurality of image capture devices to an anonymization network executing on the computer, the captured image depicting at least the specimen container and a label affixed to the specimen container, identify in the captured image the label affixed to the specimen container via the anonymization network, wherein the anonymization network is a pre-trained network trained, with training images, to identify labels on specimen containers; and edit the captured image to produce an edited image via the anonymization network to mask the identified label such that information present in the label is removed from the captured image, wherein information present in the label is removed by altering pixel data within the image.

19. The quality check module of claim 18, wherein the computer is further configured and operative via the programming instructions to:

output the edited image for segmentation or an interferent determination of a specimen in the specimen container via an HILN network executing on the computer.

20. The quality check module of claim 19, wherein the computer is further configured and operative via the programming instructions to display the edited image with the information on the label being removed from the captured image.

* * * * *